US008772551B2

(12) United States Patent
Fischer et al.

(10) Patent No.: US 8,772,551 B2
(45) Date of Patent: Jul. 8, 2014

(54) MIXED OXIDE CATALYSTS FOR CATALYTIC GAS PHASE OXIDATION

(75) Inventors: Achim Fischer, Aschaffenburg (DE); Weimin Lu, Hangzhou (CN); Christoph Weckbecker, Gründau-Lieblos (DE); Klaus Huthmacher, Gelnhausen (DE)

(73) Assignee: Evonik Degussa GmbH, Hanau-Wolfgang (DE)

( * ) Notice: Subject to any disclaimer, the term of this patent is extended or adjusted under 35 U.S.C. 154(b) by 0 days.

(21) Appl. No.: 13/177,093

(22) Filed: Jul. 6, 2011

(65) Prior Publication Data
US 2011/0263415 A1    Oct. 27, 2011

Related U.S. Application Data

(62) Division of application No. 12/445,887, filed as application No. PCT/EP2007/061062 on Oct. 17, 2007, now Pat. No. 8,222,461.

(30) Foreign Application Priority Data

Oct. 20, 2006    (CN) .......................... 2006 1 0131008

(51) Int. Cl.
C07C 45/00    (2006.01)
B01J 27/188    (2006.01)
B01J 37/04    (2006.01)
B01J 37/08    (2006.01)

(52) U.S. Cl.
USPC ........... 568/469; 502/210; 502/211; 502/305; 502/306; 502/307; 502/308; 502/311

(58) Field of Classification Search
USPC .................. 502/211, 305, 306, 307, 308, 311
See application file for complete search history.

(56) References Cited

U.S. PATENT DOCUMENTS

| 3,776,952 | A | 12/1973 | Eden et al. |
| 6,479,691 | B1 * | 11/2002 | Sasaki et al. .................. 558/321 |
| 2005/0065370 | A1 | 3/2005 | Borgmeier et al. |
| 2006/0004226 | A1 | 1/2006 | Machhammer et al. |

FOREIGN PATENT DOCUMENTS

| EP | 0995491 | 4/2000 |
| EP | 1075871 | 2/2001 |
| EP | 1147807 | 10/2001 |
| EP | 1234612 | 8/2002 |
| FR | 1447982 | 8/1966 |
| GB | 1086523 | 10/1967 |
| GB | 1286083 | 8/1972 |
| WO | 01/68894 A1 | 9/2001 |
| WO | WO 2004/105938 | 12/2004 |
| WO | 2005/083082 A1 | 9/2005 |
| WO | 2005/090589 A3 | 9/2005 |
| WO | 2006/058998 A2 | 6/2006 |
| WO | WO 2007/042369 | 4/2007 |

OTHER PUBLICATIONS

International Search Report received in PCT/EP2008/051762. Mailed Apr. 25, 2008.
International Search Report, Nov. 29, 2007.
Journal of Xiamen University (Natural Science), "MoVTeO/SiO$_2$", vol. 43, No. 2, Mar. 2004.
Redlingshofer et al., "Kinetic Modeling of the Heterogeneously Catalyzed Oxidation of Propene to Acrolein in a Catalytic Wall Reactor", Ind. Eng. Chem. Res., 2003, 42, pp. 5482-5488.
Xin et al., "Effect of Redox Properties on Selective Oxidation of Propane to Acrolein over Molybdate-Based Catalyst", Chinese Journal of Catalysis, vol. 23, No. 3, May 2002.

* cited by examiner

*Primary Examiner* — Sikarl Witherspoon
(74) *Attorney, Agent, or Firm* — Smith, Gambrell & Russell, LLP

(57) ABSTRACT

Disclosed herein are mixed oxide catalysts for the catalytic gas phase oxidation of alkanes, or mixtures of alkanes and olefins, for the production of aldehydes and carboxylic acids with air or oxygen in the presence of inert gases at elevated temperatures and pressure, and a method for the production of catalysts.

26 Claims, No Drawings

MIXED OXIDE CATALYSTS FOR CATALYTIC GAS PHASE OXIDATION

This application is a divisional of U.S. patent application Ser. No. 12/445,887, filed 16 Apr. 2009, pending now U.S. Pat. No. 8,222,461, which is herein incorporated by reference in its entirety, and which is a 371 National Phase application of PCT/EP2007/061062, having an international filing date of 17 Oct. 2007, and claims the benefit of CN 200610131008.7, filed 20 Oct. 2006.

INTRODUCTION AND BACKGROUND

The invention relates to mixed oxide catalysts and to their use for the catalytic gas phase oxidation of alkanes or mixtures of alkanes and olefins and to processes for preparing the catalysts.

In particular, the catalyst can be used to convert propane to acrolein and acrylic acid or isobutane to methacrolein and methacrylic acid, acrolein or methacrolein being formed at least as the main product. As well as the desired acrolein and acrylic acid product, the reaction of the alkane over heterogeneous catalysts with an oxygen-containing gas leads to a series of by-products: for example to the formation of $CO_2$ and CO.

It is known that the type of chemical composition of the mixed oxide (phase formation and formation of reaction sites) and also the type of physical structure (for example porosity, surface size, form of the catalyst) and the type of heat removal can greatly influence the ability to form product (selectivity) and the productivity (space-time yield). In the case of alkane oxidation, the catalyst used is generally mixed oxides which, in their chemical and physical makeup, have a complex structure.

STATE OF THE ART

The reaction of propane with oxygen or air over the known Mo—V—Te catalysts leads generally to the formation of acrylic acid. Acrolein is formed only in traces, if at all. The publications for the preparation of acrylic acid are numerous and form the subject-matter of many scientific discussions.

WO 2004105938 relates to the preparation of acrylic acid from propane using catalysts of the general formula $Te_aMo_1V_bNb_cO_x$ (I) or $Sb_a'Mo_1V_bO_y$ (I'); this forms acrolein with selectivities of 0 to 0.3%.

WO 2006058998 describes the preparation of a catalyst comprising tantalum of the general formula $MoV_aXbTa_cSi_dO_x$. The catalyst system is likewise used to prepare acrylic acid. Acrolein is formed with selectivities of less than 1% as a by-product.

From U.S. 2005065370 is a process for preparing meth(acrylic acid) by the conversion of saturated hydrocarbons over a mixed oxide catalyst which comprises the elements Mo and V, and at least Te and Sb, and also one of the elements Nb, Ta, W, Ce and Ti, by virtue of the catalyst bed being interrupted by a further catalyst bed which consists of a mixed oxide catalyst comprising the elements Mo, Bi and Fe. In the examples, only statements about the acrylic acid selectivity are made.

Xiamen Daxue Xuebao, Ziran Kexueban (2004), 43(2), 203-207 describes the conversion of propane to acrolein over Mo—V—Te catalysts; in this case, propane conversions around 20% and acrolein selectivities of up to 30% are obtained. Cuihua Xuebao (2002), 23(3), 281-284 describes conversions of propane to acrolein over $Ag_{0.3}MoP_{0.6}O$ and $Ce_{0.1}Ag_{0.3}MoP_{0.6}O_y$.

According to U.S. 2006004226, acrolein and acrylic acid are formed by converting propane over two reaction zones (catalysts). In the first stage, a mixture of propane and propene is formed; after the second stage, the condensate contains, inter alia, 98.48% by weight of acrylic acid and 0.002% by weight of acrolein.

SUMMARY OF THE INVENTION

The present invention has for its object to provide a process for preparing aldehydes, in which especially acrolein or else mixtures of acrolein and acrylic acid are formed in good yields from propane or from propane/propene mixtures by oxidation with oxygen. The oxidation is optionally performed in the presence of inert gases, steam or offgases at elevated temperatures and in the presence of a heterogeneous mixed oxide catalyst.

The alkane or the mixture of alkane and olefin is converted to the aldehyde and acid oxidation products at elevated temperature and a ratio between alkane, oxygen, inert gas(es) and water of generally 1:0.5-5:0-10:0-18. In a preferred embodiment, the water content is 0.

The inert gases which can be used are all gaseous compounds which behave inertly under the oxidation conditions described. For example, these may be nitrogen, helium or mixtures thereof. It is likewise possible to feed the "return gas" from the reactor back in.

The invention provides mixed oxide catalysts of the general formula $$(Mo_1A_aB_bC_cD_dE_eF_fG_g)O_x \quad (I)$$

in which:
A: bismuth,
B: at least one of the elements comprising nickel and/or cobalt,
C: at least one of the elements comprising Fe, Ce, Mn, Cr, V,
D: at least one of the elements comprising W, P,
E: at least one of the elements comprising Li, K, Na, Rb, Cs, Mg, Ca, Ba, Sr,
F: at least one of the elements comprising Zn, Nb, Se, Te, Sm, Gd, La, Y, Pd, Pt, Ru, Ag, Au,
G: at least one of the elements comprising Si, Al, Ti, Zr and
a=0-1, preferably 0-0.1,
b=0-1, preferably 0-0.1,
c=0.001-1, preferably 0.005-0.1,
d=0.01-2, preferably 0.01-0.1,
e=0-1, preferably 0-0.1,
f=0.01-1.5, preferably 0.01-0.8,
g=0-800,
x=number which is determined by the valency and frequency of the elements other than oxygen.

The letters a to x represent the atomic ratios of the corresponding elements in relation to Mo.

Catalysts of the general formula I are particularly suitable catalytically active solids, for example for the conversion of propane or mixtures of propane and propene to acrolein and acrylic acid, and are provided by a process which likewise forms part of the subject-matter of the invention. Particularly advantageously, the reaction is performed in reactors which allow the catalyst to be used as a fixed bed or fluidized bed. However, it is likewise possible to apply the catalyst to the wall of the reaction chamber. At this point, it should be noted that catalysts of the general formula I can also be utilized for the conversion of isobutane or mixtures of isobutane and isobutene to methacrolein and methacrylic acid.

DETAILED DESCRIPTION OF THE INVENTION

In the processes known from the prior art, proceeding from suitable sources of the components of the multimetal oxide composition, a very intimate, preferably finely divided, dry mixture is obtained and is treated thermally at temperatures of >150 to 700° C., preferably 400 to 700° C. or especially 450 to 600° C. The thermal treatment can in principle be effected either under an oxidizing atmosphere or under an inert atmosphere and optionally in the presence of steam. Useful oxidizing atmospheres include, for example, air, air enriched with molecular oxygen or air depleted of oxygen. However, preference is given to performing the thermal treatment under inert atmosphere, i.e., for example, under molecular nitrogen and/or noble gas. Typically, the thermal treatment is effected at standard pressure (1 atm). It will be appreciated that the thermal treatment can also be effected under reduced pressure or under elevated pressure.

Overall, the thermal treatment may take from 0.25 h up to 24 h or more and be effected in several steps. Preference is given to 0.25 to 10 h.

Preference is given to effecting the thermal treatment of the dry mixture under inert atmosphere at a temperature of >150 to 400° C. or 250 to 450° C. (=predecomposition step). Thereafter, the thermal treatment is appropriately continued under inert gas at temperatures of >450 to 700° C., in particular 450 to 600° C.

Should a shaping be required, it is advantageous to interrupt the thermal treatment in the temperature range of 420 to 490° C., to perform the shaping and then to continue the thermal treatment in the temperature range of 490 to 700° C., especially up to 600° C. However, it is also possible to shape the finished calcined powder.

The starting compounds can be mixed intimately in dry or in wet form.

When the preparation is effected in wet form, the starting compounds are mixed with one another in the form of aqueous solutions and/or suspensions. Subsequently, the mixture is generally dried at 60° C. to <150° C., especially up to 130° C., and treated thermally after the drying.

Useful sources for the for the constituents of the mixed oxide catalyst of the formula (I) may, in the performance of the above-described preparation method, be all of those which are capable of forming oxides and/or hydroxides in the course of heating (optionally under air). Of course, such starting compounds used may also partly or exclusively already be oxides and/or hydroxides of the elemental constituents.

The components are ideally dissolved in the form of their compounds selected from the group of ammonium compounds, oxalates, hydroxides, carbonates, phosphates, acetates, carbonyls and/or nitrates, individually or together, and mixed with one another. Particular preference is given to carbonates, nitrates and phosphates or mixtures thereof. It is likewise possible to use acids of the salts, for example nitric acid, phosphoric acid or carbonic acid, or suspensions of the corresponding metal oxides.

Depending on the type of metal salts which are used in the precipitation, it may be necessary to add salts and acids or mixtures thereof to the precipitation mixture. Ideally, ammonia or ammonium salts are used here, for example ammonium carbonate, ammonium heptamolybdate or metal nitrates, for example cobalt nitrate; it is likewise possible to use the corresponding acids, for example nitric acid in the amounts needed to establish the ionic ratio. The pH during the precipitation is typically <8, especially <7.

Likewise of significance is the temperature of the precipitation solution. It may thus be that the later activity of the catalyst is reduced significantly in the case of too high a temperature. The precipitation can in principle be performed at temperatures of 25 to 90° C.

The coprecipitate can be precipitated in one stage. Particular preference is given to performing the precipitation in several stages by stepwise addition of the individual components or mixtures thereof. The number of precipitation stages is not limited in principle. However, preference is given to 1 to 3 precipitation stages.

The resulting suspension can be processed further directly, or it is advantageously allowed to mature for >0 to 24 hours. Preference is given to >0 to 12 hours, particular preference to 0 to 6 hours. It is obvious that the precipitation suspension is homogenized before the further processing, for example by stirring.

After the maturation, the liquid of the suspension can be removed by evaporation, centrifugation or filtration. It is likewise possible to evaporate the liquid and simultaneously to dry the solid, which can be done, for example, by spray-drying. The liquid should be evaporated at a temperature of 80 to 130° C. The solid can be dried with air, oxygenous inert gases or inert gases, for example nitrogen. When the drying is performed in an oven, the temperature should be between 100 and 150° C. In a spray dryer, the starting temperature of the drying medium should be 200 to 500° C., and a temperature on deposition of the dried powder of 80 to 200° C. should be provided. The resulting particles should preferably have a particle size distribution of 15 to 160 μm with a mean particle diameter between 15 and 80 μm.

The dried powder can in principle be calcined in a wide variety of different oven types, for example in a forced-air oven, rotary tube, tray oven, shaft oven or belt oven. The control quality and the quality of temperature detection of the oven should be as high as possible. The residence time of the powder in the oven should, according to the oven type, be between 0.25 and 10 h.

It is likewise possible to perform the calcination and the thermal decomposition of the salts which occurs at the same time in one or more stages. It is possible to utilize temperatures of 200 to 650° C., especially 300° to 650°. The thermal decomposition can be performed with addition of inert gas, composed of mixtures of oxygen with an inert gas.

The inert gases usable are, for example, nitrogen, helium, steam or mixtures of these gases.

After the thermal treatment, the resulting catalyst material can appropriately be comminuted and optionally classified.

The powder thus obtained is suitable as a catalyst. For industrial use, it is particularly appropriate, after addition of commercial shaping media and binders, to shape the powder. This can be done by tabletting, extrusion or by coating a support. In this context, the geometric shape of the support is not limiting. Instead, it is guided by the requirements of the reactor (for example tube diameter, length of the catalyst bed). For example, the support may be a pyramid, a cylinder, a saddle, a sphere, a ring or a polygon, but it may also be a wall of the reactor in which the conversion of the reactants takes place.

Useful materials for the support bodies in accordance with the invention include especially aluminium oxide, titanium oxide, silicon dioxide, silicates such as clay, kaolin, pumice, aluminium silicate and magnesium silicate, silicon carbide and zirconium oxide.

The surface of the support body may either be smooth or rough. Advantageously, the surface of the support body is rough.

The thickness of the active oxide composition coating present on the coated catalysts is typically 10 to 1000 μm. It may, though, also be 50 to 700μ, 100 to 600μ, or 150 to 400μ. Possible coating thicknesses are also 10 to 500 μm, 100 to 400 μm or 150 to 300 μm.

The binders used may be various oils, polyols, for example glycerol and polyvinyl alcohols, celluloses, saccharides, acrylates and alkyl derivatives, mixtures or condensates thereof. In a shaping of the catalyst powder, the catalyst should preferably be aftertreated thermally in the temperature range of 490 to 650° C., such that the active composition for use in industrial reactors solidifies.

The invention likewise provides a process for oxidation of alkanes and mixtures of alkanes/olefins to prepare unsaturated aldehydes, with or without the corresponding acids, in the presence of the inventive catalysts.

The olefins differ by one double bond from the alkanes used in each case.

The inventive reaction to prepare acrolein or optionally mixtures of acrolein and acrylic acid is performed generally at temperatures of 350-500° C. and a pressure of 1.0-2.2 bara. The reactants, alkane or a mixture of alkane and olefin, are converted to the oxidation products, aldehyde, with or without acid, at relatively high temperatures and a ratio between alkane, oxygen, inert gas(es) and water of preferably 1:0.5-5:0-10:0-15, at a loading with 2-20 mol of alkane or of a mixture of alkane and olefin/l of catalyst bed/h.

Instead of inert gas, the offgas from the reaction, from which the condensable constituents have been removed, can be used. Particularly good results are obtained in the case of use of tube bundle reactors, plate reactors (for example EP 0 995 491; EP 1 147 807) or wall reactors (for example Redlingshoefer H., Fischer A., et al., Ind. Eng. Chem. Res. 2003, 42, 5482-5488; EP 1 234 612), in which the catalyst has been applied to the wall.

The internal diameter of the reaction tubes or the distance between the plates should be 18 to 28 mm, preferably 20 to 26 mm; the wall thickness of the iron-containing steel should be between 1 and 3.5 mm. A typical reactor length is 3.00 to 4.00 m. The catalyst is preferably used homogeneously over the reactor length without dilution with shaped diluent bodies; of course, the application may necessitate dilution, for example with shaped inert bodies.

The inventive catalysts, even at high specific loading, have an improved activity and selectivity for the preparation of acrolein.

The invention will be explained with reference to working examples. Definitions used are:

the yield (%) of the product as (mol/h of product formed)/(mol/h of reactant supplied)×100 the conversion of the alkane (%) as

[1−(mol/h of alkane leaving the reaction tube)/(mol/h of alkane entering the reaction tube)]×100 the selectivity (%) as (yield of the product/conversion)×100

The invention detailed is, in order to improve understanding, described by the examples which follow, but is not restricted to these examples.

EXAMPLES

Example 1

A solution I was prepared by dissolving 2118.6 g of ammonium heptamolybdate in 2.7 l of water at 80° C. A solution II was obtained at 80° C. by dissolving the desired amount of $H_2TeO_4.2H_2O$ and cobalt nitrate. The two solutions were combined with stirring and the slurry (suspension) which formed was concentrated to dryness. The still moist powder obtained was dried at 150° C. and converted to the oxides at a temperature of 600° C. The mixed metal oxide powder obtained has the composition $(MoCo_{0.1}Te_{0.2})O_x$.

Example 2

The catalyst of Example 1 was contacted with a mixture of the composition of one part of propane (chemical grade) (50% of the total amount of the mixture) and one part of oxygen (50% of the total amount of the mixture). The space velocity which arose was 3000 $h^{-1}$. The temperature of the heat carrier was 450° C. The conversion of the propane was 48.9 mol %; the product selectivity for acrolein was 32%.

Example 3

A solution I was prepared by dissolving 2118.6 g of ammonium heptamolybdate in 2.7 l of water at 80° C. A solution II was obtained at 80° C. by dissolving the desired amount of bismuth(III) nitrate and chromium(III) nitrate. The two solutions were combined with stirring and the slurry which formed was concentrated to dryness. The still moist powder obtained was dried at 150° C. and converted to the oxides at a temperature of 600° C. The mixed metal oxide powder obtained has the composition $(MoCr_{0.0286}Bi_{0.05})O_x$.

Example 4

The catalyst of Example 3 was contacted with a mixture of the composition of one part of propane (chemical grade) and one part of oxygen. The space velocity which arose was 3000 $h^{-1}$. The temperature of the heat carrier was 500° C. The conversion of the propane was 38 mol %; the product selectivity for acrolein was 43%.

Example 5

The product gas of Example 4 was recycled and converted over the catalyst of Example 3. The space velocity which arose was 3000 $h^{-1}$. The temperature of the heat carrier was 500° C. The conversion of the propane was 76 mol %; the product yield of acrolein was 33%.

Example 6

A solution I was prepared by dissolving 2118.6 g of ammonium heptamolybdate in 2.7 l of water at 80° C. A solution II was obtained at 80° C. by dissolving the desired amount of chromium(III) nitrate and $H_2TeO_4.2H_2O$. The two solutions were combined with stirring and the slurry which formed was concentrated to dryness. The still moist powder obtained was dried at 150° C. and converted to the oxides at a temperature of 600° C. The mixed metal oxide powder obtained has the composition $(MoCr_{0.0286}Te_{0.05})O_x$.

Example 7

The catalyst of Example 6 was contacted with a mixture of the composition of one part of propane (chemical grade) and one part of oxygen. The space velocity which arose was 3000 $h^{-1}$. The temperature of the heat carrier was 450° C. The conversion of the propane was 27.5 mol %; the product selectivity for acrolein was 58%.

Example 8

A solution I was prepared by dissolving 2118.6 g of ammonium heptamolybdate in 2.7 l of water at 80° C. A solution II was obtained at 80° C. by dissolving the desired amount of chromium(III) nitrate, $H_3PO_4$ and $H_2TeO_4.2H_2O$. The two solutions were combined with stirring and the slurry which formed was concentrated to dryness. The still moist powder obtained was dried at 150° C. and converted to the oxides at a temperature of 600° C. The mixed metal oxide powder obtained has the composition $(MoCr_{0.0286}Te_{0.05}P_{0.05})O_x$.

Example 9

The catalyst of Example 8 was contacted with a mixture of the composition of one part of propane (chemical grade) and one part of oxygen. The space velocity which arose was 3000 $h^{-1}$. The temperature of the heat carrier was 450° C. The conversion of the propane was 30 mol %; the product selectivity for acrolein was 70%.

Example 10

A solution I was prepared by dissolving 2118.6 g of ammonium heptamolybdate in 2.7 l of water at 80° C. A solution II was obtained at 80° C. by dissolving the desired amount of chromium(III) nitrate, cobalt(II) nitrate and $H_2TeO_4.2H_2O$. The two solutions were concentrated with stirring and the slurry which formed was concentrated to dryness. The still moist powder obtained was dried at 150° C. and converted to the oxides at a temperature of 600° C. The mixed metal oxide powder obtained has the composition $(MoCr_{0.0286}Te_{0.05}Co_{0.15})O_x$.

Example 11

The catalyst of the composition $(MoCr_{0.0286}Te_{0.05}Co_{0.8})O_x$ was contacted with a mixture of the composition of 1.2 parts of propane (chemical grade) and one part of oxygen. The space velocity which arose was 3000 $h^{-1}$. The temperature of the heat carrier was 450° C. The conversion of the propane was 18 mol %; the product selectivity for acrolein was 72%.

The invention claimed is:

1. A mixed oxide catalyst of the formula $$(MoA_aB_bC_cD_dE_eF_fG_g)O_x \quad (I)$$

in which:
A: bismuth,
B: at least one of the elements comprising nickel and/or cobalt,
C: at least one of the elements comprising Fe, Ce, Mn, Cr, V,
D: at least one of the elements comprising W, P,
E: at least one of the elements comprising Li, K, Na, Rb, Cs, Mg, Ca, Ba, Sr,
F: at least one of the elements comprising Zn, Nb, Se, Te, Sm, Gd, Y, Pd, Pt, Ru, Ag, Au,
G: at least one of the elements comprising Si, Al, Ti, Zr and
a=0
b=0-0.1
c=0.005-0.1
d=0.01-0.1
e=0-1
f=0.01-0.8
g=0-800,
x=number which is determined by the valency and frequency of the elements other than oxygen.

2. Mixed oxide catalyst according to claim 1, wherein the pulverulent mixed oxide catalyst has been applied to inert support materials or is extruded as a bulk material.

3. Process for preparing the mixed oxide catalyst of claim 1 comprising:
mixing solutions of compounds of the elements present in the mixed oxide catalyst of the formula I, preparing coprecipitates thereof, and resulting pulverulent solid is isolated, dried, treated thermally and optionally shaped.

4. Process according to claim 3, wherein pH during preparation of the coprecipitate(s) is <8.

5. Process according to claim 3, wherein compounds of the elements present in the catalyst of the formula (I) are selected from the group consisting of ammonium or amine compounds, oxalates, carbonates, phosphates, acetates, carbonyls, hydroxides, oxides or nitrates, and mixtures thereof, are used.

6. Process according to claim 3, wherein carbonates, hydroxides, oxides, nitrates phosphates and mixtures of these salts are used.

7. Process according to claim 3, wherein anions of acids corresponding to the salts are used.

8. Process according to claim 3, wherein ammonium carbonate, ammonium heptamolybdate and at least one metal nitrate including chromium(III) nitrate, bismuth nitrate, cobalt nitrate; and/or nitric acid are used to prepare the coprecipitate.

9. Process according to claim 3, precipitation is performed at temperatures of 5 to 90° C.

10. Process according to claim 9, wherein precipitation is performed at temperatures of 20 to 90° C.

11. Process according to claim 3, wherein a suspension is obtained by precipitation is matured for >0 to 24 hours.

12. Process according to claim 3, wherein the coprecipitate is removed and dried.

13. Process according to claim 3, wherein dried coprecipitate, before the calcination, consists of spray-dried particles having a particle size distribution of 15 to 160 μm.

14. Process according to claim 13, the dried coprecipitate has a mean particle size distribution of between 15 μm and 80 μm.

15. Process according to claim 13, wherein residence time of dried powder in a thermal treatment oven is between 0.25 and 13 hours, in the course of which temperatures of >150 to 700° C. are established.

16. Process according to claim 3, wherein the thermal treatment is performed in one or more stages.

17. Process according to claim 15, wherein the thermal treatment is performed in an atmosphere composed of inert gas, composed of mixtures of oxygen with an inert gas and/or in the presence or absence of steam.

18. Process according to claim 3, wherein thermally treated powder is shaped by tabletting, extrusion, or applied to a support.

19. Process according to claim 3, wherein, after the catalyst in the form of a powder has been shaped, shaped body thus obtained is heat-treated within a temperature range of 450 to 650° C.

20. Mixed oxide catalyst according to claim 1, wherein (i) C is Cr, (ii) F is Te, or (iii) C is Cr and F is Te.

21. Process for preparing the mixed oxide catalyst of claim 1 comprising:

mixing solutions of compounds of the e elements present in the mixed oxide catalyst of the formula I, preparing coprecipitates thereof, and resulting pulverulent solid is isolated, dried, treated thermally and optionally shaped.

22. Process for preparing the mixed oxide catalyst of claim 20 comprising:
mixing solutions of compounds of the e elements present in the mixed oxide catalyst of the formula I, preparing coprecipitates thereof, and resulting pulverulent solid is isolated, dried, treated thermally and optionally shaped.

23. A mixed oxide catalyst of the formula $$(MoA_aB_bC_cD_dE_eF_fG_g)O_x \qquad (I)$$

in which:
A: bismuth,
B: at least one of the elements comprising nickel and/or cobalt,
C: Cr
D: P,
E: at least one of the elements comprising Li, K, Na, Rb, Cs, Mg, Ca, Ba, Sr,
F: Te,
G: at least one of the elements comprising Si, Al, Ti, Zr, and
a=0
b=0-0.1
c=0.005-0.1
d=0.01-0.1
e=0-1
f=0.01-0.8
g=0-800,
x=number which is determined by the valency and frequency of the elements other than oxygen.

24. The mixed oxide catalyst of claim 23 having the formula $(MoC_cD_dF_f)O_x$.

25. The mixed oxide catalyst of claim 23, wherein the atomic ratio of C to Mo is 0.0286, the atomic ratio of D to Mo is 0.05, and the atomic ratio of F to Mo is 0.05.

26. The mixed oxide catalyst of claim 24, wherein the atomic ratio of C to Mo is 0.0286, the atomic ratio of D to Mo is 0.05, and the atomic ratio of F to Mo is 0.05.

* * * * *